United States Patent
Hayzelden

(10) Patent No.: US 6,730,058 B2
(45) Date of Patent: May 4, 2004

(54) ADJUSTABLE PROFILE STEERABLE CATHETER

(75) Inventor: Robert C. Hayzelden, Canyon Lake, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 82 days.

(21) Appl. No.: 09/952,501

(22) Filed: Sep. 13, 2001

(65) Prior Publication Data

US 2003/0050598 A1 Mar. 13, 2003

(51) Int. Cl.$^7$ .............................................. A61M 31/00
(52) U.S. Cl. ................. 604/95.04; 604/95.01; 606/146; 606/149
(58) Field of Search ................. 600/146, 147, 600/148, 149, 150, 151; 607/115, 116, 119, 122, 123; 606/45, 46, 48, 49, 47; 604/95.01, 95.02–95.03, 95.04–95.05, 528

(56) References Cited

U.S. PATENT DOCUMENTS

| | | | |
|---|---|---|---|
| 5,358,478 A | * | 10/1994 | Thompson et al. ...... 604/95.04 |
| 5,487,757 A | | 1/1996 | Truckai et al. |
| 5,489,270 A | | 2/1996 | van Erp |
| 5,531,686 A | | 7/1996 | Lundquist et al. |
| 5,588,964 A | | 12/1996 | Imran et al. |
| 5,935,102 A | | 8/1999 | Bowden et al. |
| 6,035,224 A | | 3/2000 | West |

* cited by examiner

*Primary Examiner*—Brian L. Casler
*Assistant Examiner*—Kevin C. Sirmons
(74) *Attorney, Agent, or Firm*—Fulwider Patton Lee & Utecht, LLP

(57) ABSTRACT

A catheter includes a steering system for manipulating the distal-end region of a sheath having a plurality of electrodes into direct contact with difficult-to-reach areas of the human body. The steering system includes a core base, a core distal tip, a stylet, a steering tendon, and a lever. Movement of the lever applies tension to the steering tendon causing the distal end of the sheath to deflect. A positioning mechanism, including a slidable controller, adjusts the position of the steering system relative to the catheter sheath to thereby provide multiple steering profiles.

11 Claims, 7 Drawing Sheets

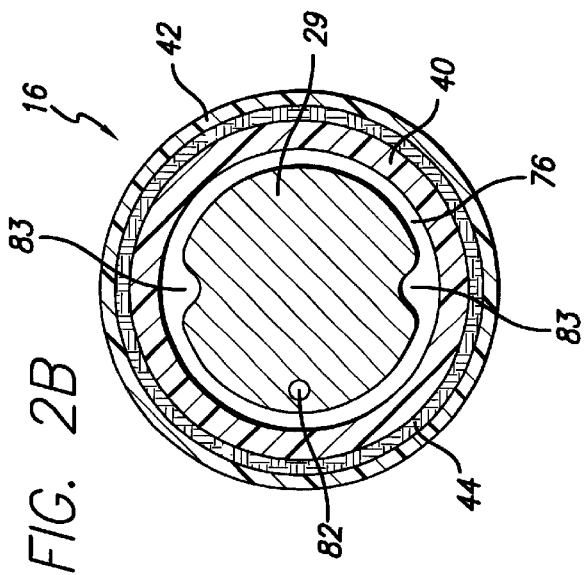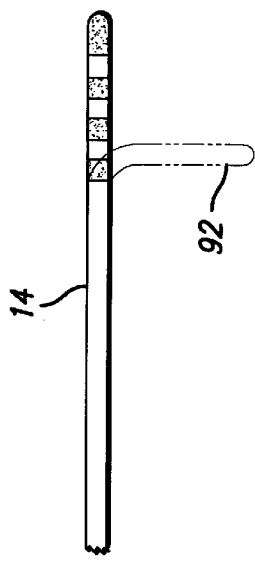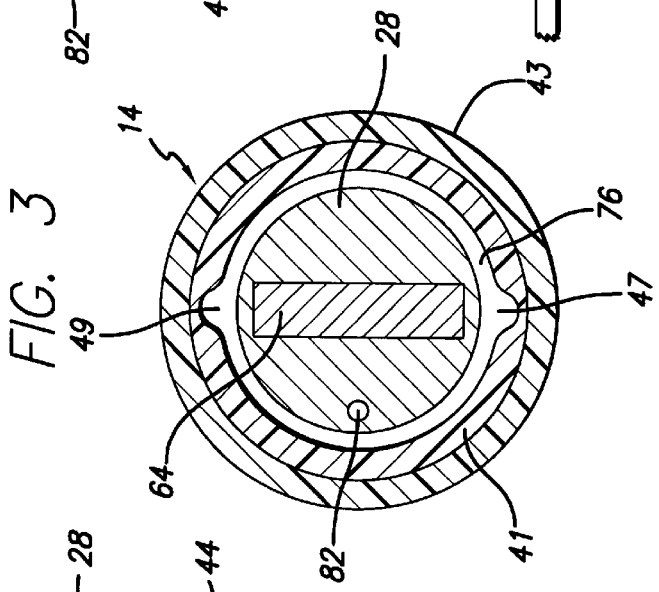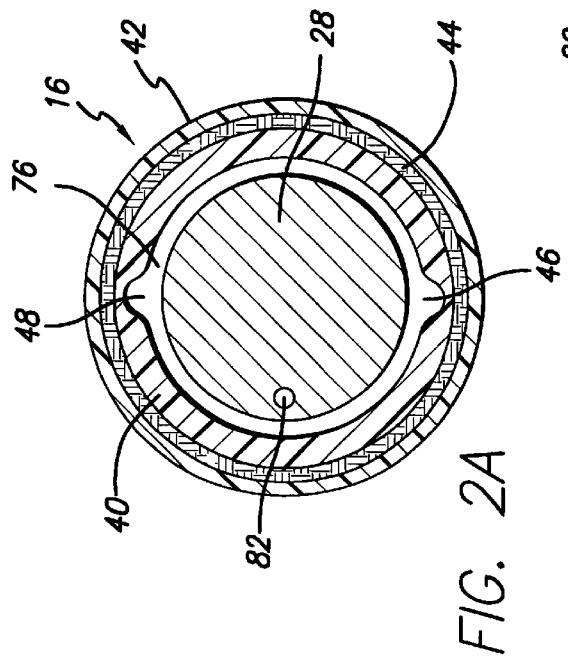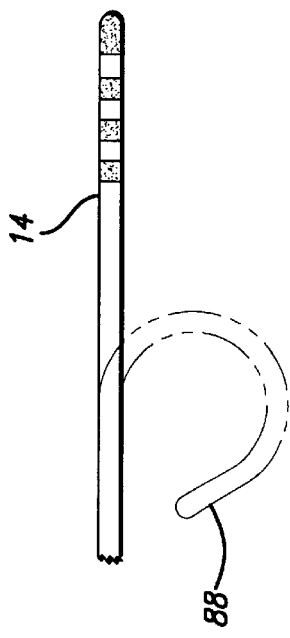

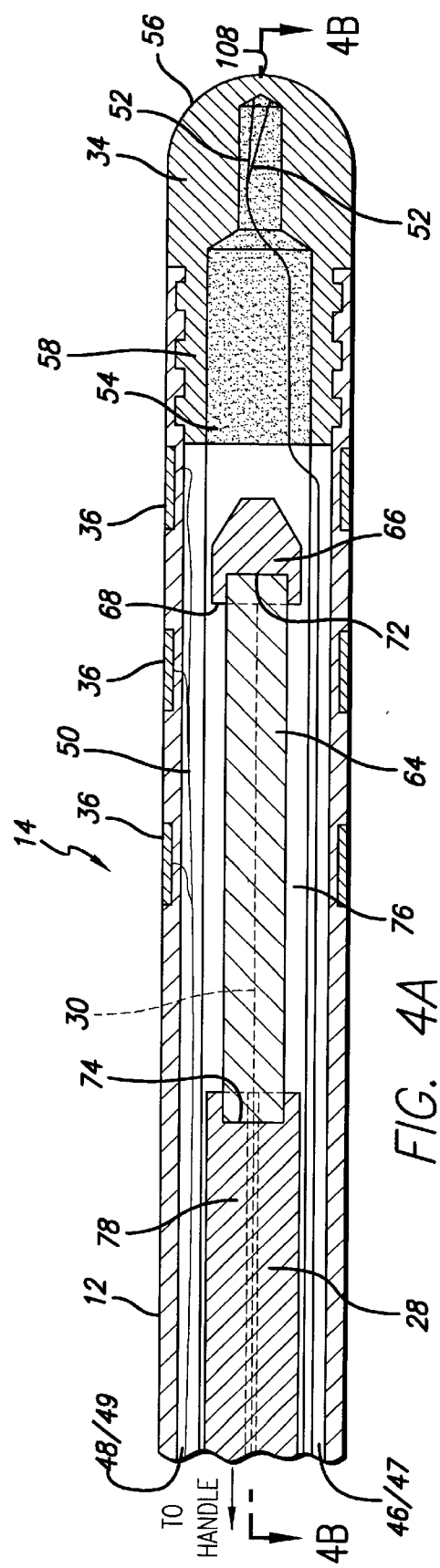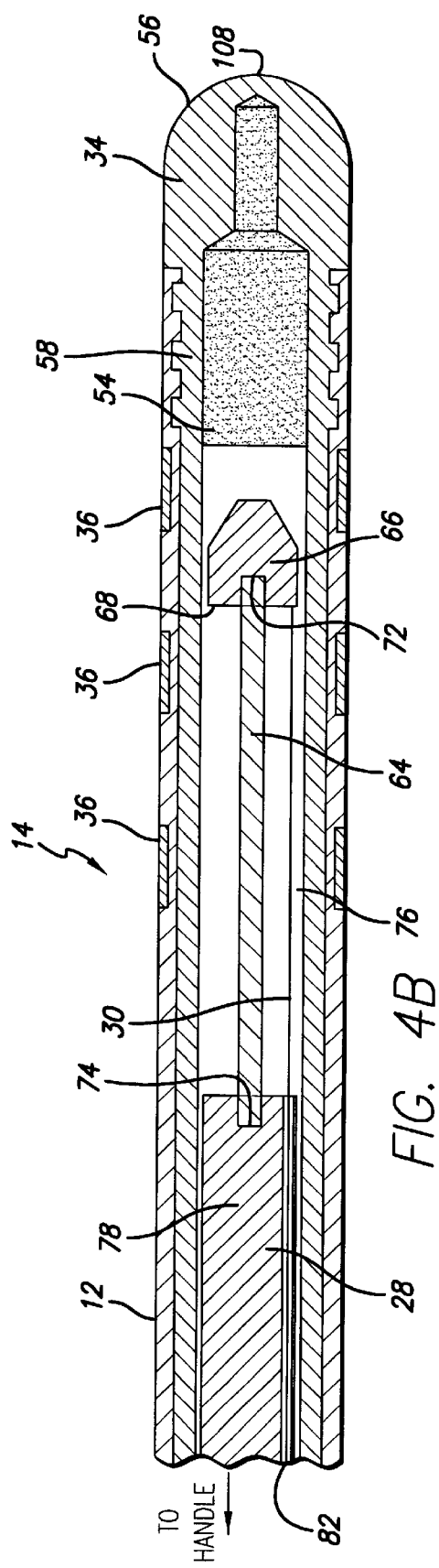

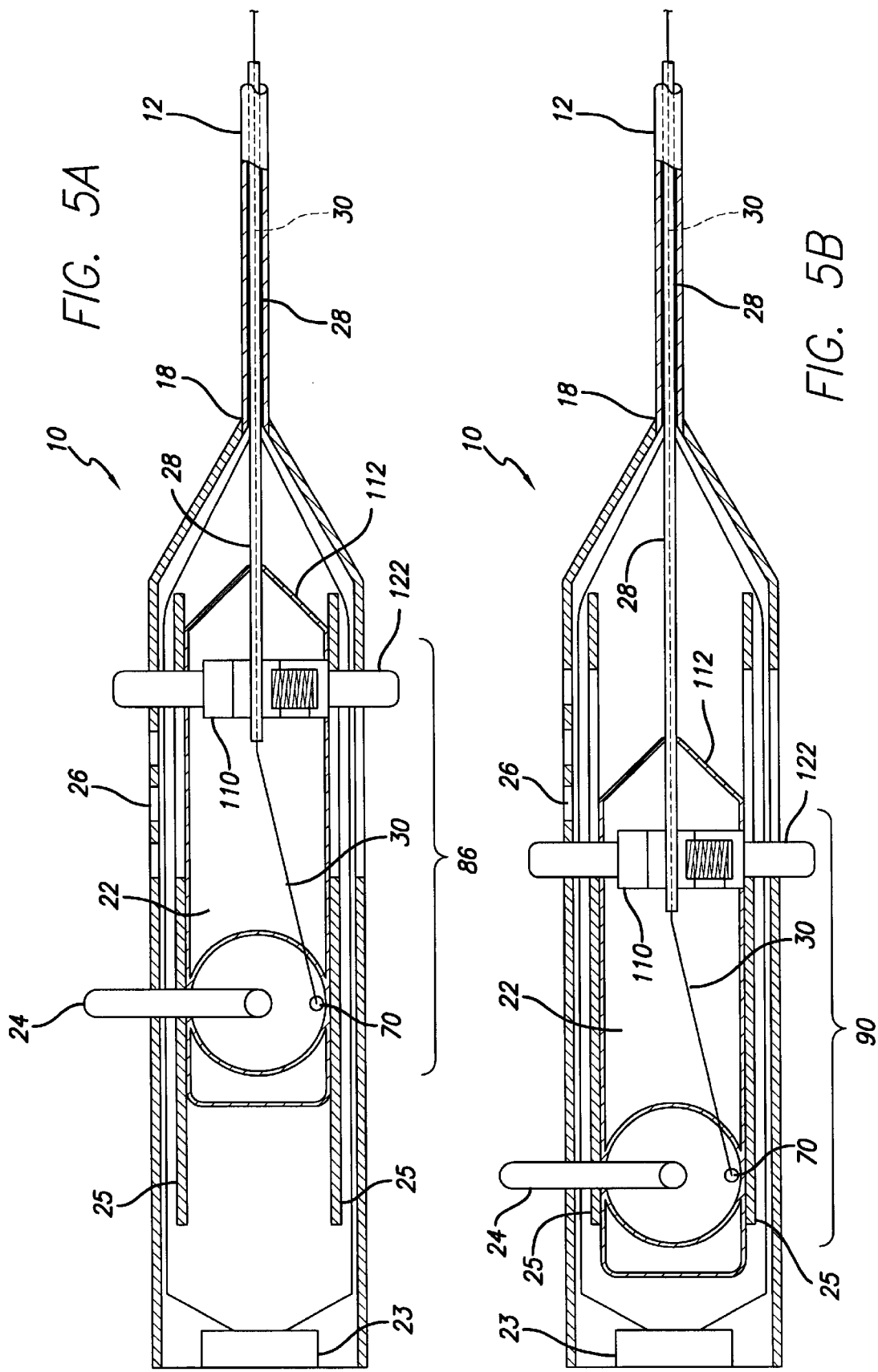

ADJUSTABLE PROFILE STEERABLE CATHETER

BACKGROUND OF THE INVENTION

1. Field of the Invention

This invention relates generally to steerable catheters. More particularly, the invention relates to a steerable catheter with a movable steering system for deflecting the distal-end region of the catheter in a variety of different profiles.

2. Description of the Related Art

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

One such EP catheter system, as disclosed in U.S. Pat. Nos. 6,059,778 and 6,096,036, includes a plurality of spaced apart band electrodes located at the distal end of the catheter and arranged in a linear array. The band electrodes are positioned proximal heart tissue. RF energy is applied through the electrodes to the heart tissue to produce a series of long linear lesions similar to those produced by the Maze procedure. The catheters currently used for this procedure are typically flexible at the distal end, and the profile at the distal end is adjustable. However, when using such catheters, it is often difficult to conform the distal end profile to some of the irregular topographies of the interior cavities of the heart. In other instances, it is difficult for a multi-electrode catheter that is designed to produce long linear lesions to access and ablate tissue in regions that require short linear lesions, such as the so-called isthmus region that runs from the tricuspid annulus to the eustachian ridge. Ablation of tissue in this region, and other regions non-conducive to the placement of multi-electrode, long, linear-lesion ablation catheters within them, is best accomplished by delivering RF energy to a tip electrode to produce localized spot lesions or tip-drag lesions.

Proposed methods of ablating irregular topography areas and regions, such as the isthmus region, use a rigid introducer sheath in combination with a tip-electrode ablation catheter. The introducer sheath is used to position the tip electrode in the proper location. Once positioned, the electrode is either held in place by the sheath to produce a spot lesion or is dragged along the surface of the tissue, by the sheath, to produce a tip-drag lesion. The disadvantage of this system is that it requires the use of two instruments: the introducer sheath and the catheter. The use of an introducer sheath increases both instrument cost and patient trauma.

Other catheters for producing spot lesions or tip-drag lesions typically comprise a tip ablation electrode and a plurality of mapping band electrodes positioned at the distal end of the catheter. The catheters are steerable in that they are configured to allow the shape of the distal end of the catheter to be manipulated from a location outside the patient's body. Steerable catheters that produce multiple bending profiles provide a broader range of steerability. However, known steerable catheters such as that disclosed in U.S. Pat. No. 5,195,968 have steering tendons attached to a ribbon, at or near the longitudinal centerline of the catheter. Because these tendons are fixed in place, the catheter is capable of providing only two types of steering profiles. As such, its ability to ablate within a biological site having cavities of various different shapes and sizes is limited.

Hence, those skilled in the art have identified a need for a catheter having a steerable distal-end region that is not limited to a select few deflection profiles but rather a variety of different profiles to improve access to difficult-to-reach locations of the human body. The present invention fulfills these needs and others.

SUMMARY OF THE INVENTION

Briefly, and in general terms, the present invention is directed to an electrophysiological ("EP") catheter with a steerable, multi-profile distal-end region for maneuvering through and positioning within irregular topographic and difficult-to-reach locations of the human body.

In a first aspect, the invention relates to a catheter having a sheath with a proximal end, a distal-end region, and a lumen therebetween. The catheter also includes a steering system for deflecting the distal-end region and a positioning mechanism for adjusting the position of the steering system relative to the sheath. By providing a positioning mechanism that adjusts the position of the steering system, the present invention allows for the catheter flexible distal-end region to assume numerous different profiles to improve accessibility to difficult-to-reach locations of the human body.

In a detailed aspect of the invention, the steering system includes a core. The core is slidably disposed within the lumen and has a distal end positioned in the distal-end region of the sheath. The steering system also includes a lever located at the proximal end of the sheath and a tendon located within the lumen. The tendon has a first end attached to the core distal end and a second end attached to the lever. In a further detailed aspect, the core includes a distal tip and the first end of the tendon is attached thereto. In yet another detailed aspect, the core further includes a core base proximal the distal tip and a stylet extending between the core base and the core distal tip. In still another detailed facet, the core distal tip is fixed to the distal end of the stylet and the proximal end of the stylet is fixed to the distal end of the core base. In other detailed facets, the positioning mechanism may adjust the steering system to an advanced position to effect deflection at the distal end of the sheath distal-end region, or to a retracted position to effect deflection at the proximal-end region of the sheath distal-end region.

In another detailed facet, the positioning mechanism includes a handle having a proximal-end region and a distal-end region with the steering system core fixed thereto. The positioning mechanism also includes a cap that is fixed to the proximal end of the sheath. The cap is movable longitudinally along the distal-end region of the handle. In a further detailed facet, the cap includes a locking mechanism for locking the cap in place relative to the handle. In another further detailed facet, the distal-end region of the handle carries a plurality of recesses that interact with the locking mechanism.

In another detailed facet, the positioning mechanism includes a handle having the proximal end of the sheath fixed thereto. The positioning mechanism also includes a controller that is carried by the handle and attached to the core. The controller is movable longitudinally along the distal-end region of the handle. The positioning mechanism further includes a locking element that is carried by the handle and fixed to the core. The locking element is movable longitudinally along the distal-end region of the handle. The locking element is housed within the handle and is locked and released by a spring-loaded button that can engage in various locking positions. In yet another detailed facet, the distal-end region of the handle carries a plurality of positioning slots that interact with the locking element.

In a second aspect, the invention relates to a catheter having a sheath with a proximal end, a distal-end region and a lumen therebetween. The catheter also includes a core slidably disposed within the lumen with a distal end positioned in the distal-end region of the sheath. A tendon is located within the lumen and has a first end attached to the core distal end and a second end exiting the proximal end of the sheath. The catheter further includes a handle having the proximal end of the sheath fixed thereto, and a controller with a lever having the proximal end of the tendon attached and movable to effect axial displacement of the tendon. The controller, carried by the handle and attached to the core, is movable longitudinally along the distal-end region of the handle.

In a detailed aspect of the invention, longitudinal movement of the controller in the distal direction advances the core in the distal direction. In another detailed aspect, longitudinal movement of the controller in the proximal direction retracts the core in the proximal direction.

In a third aspect, the invention relates to a catheter having a sheath with a proximal end, a distal-end region, and a lumen therebetween. The catheter also includes a core. The core is slidably disposed within the lumen and has a proximal end and a distal end positioned in the distal-end region of the sheath. A tendon is located within the lumen and has a first end attached to the core distal end and a second end exiting the proximal end of the sheath. The catheter further includes a handle with a lever having the proximal end of the tendon attached and movable to effect axial displacement of the tendon. The handle has a proximal-end region and a distal-end region and the core fixed thereto. An adjustable cap is fixed to the proximal end of the sheath with the cap movable longitudinally along the distal-end region of the handle.

In a detailed aspect of the invention, longitudinal movement of the cap in the distal direction advances the sheath in the distal direction. In another detailed aspect, longitudinal movement of the cap in the proximal direction retracts the sheath in the proximal direction.

In yet another detailed aspect, the cap includes a locking mechanism for locking the cap in place relative to the handle. In another detailed aspect, the distal-end region of the handle carries a plurality of recesses that interact with the locking mechanism.

These and other aspects and advantages of the invention will become apparent from the following detailed description and the accompanying drawings, which illustrate by way of example the features of the invention.

BRIEF DESCRIPTION OF THE DRAWINGS

FIG. 2A is a section view of the construction of the proximal region of the sheath, taken along the line 2—2 from FIG. 1.

FIG. 2B is a section view of an alternative construction of the proximal region of the sheath, taken along the line 2—2 from FIG. 1.

FIG. 3 is a section view of the construction of the distal-end region of the sheath, taken along the line 3—3 from FIG. 1.

FIG. 4A is a cross section view of the distal portion of the catheter of FIG. 1 depicting detailed components of the catheter steering system in a fully advanced position.

FIG. 4B is a downward view of the distal portion of the catheter, taken along the line 4B—4B from FIG. 4A, depicting detailed components of the catheter steering system.

FIG. 5A is a cross section of the catheter handle of FIG. 1 depicting a fully advanced position of the positioning mechanism and steering system along the length of the handle.

FIG. 5B is a cross section of the catheter handle of FIG. 1 depicting a fully retracted position of the positioning mechanism.

FIG. 8 is a schematic depicting the profile created within the distal-end region of the catheter when the steering system is in a fully advanced position such as shown in FIG. 4A.

FIG. 9 is a schematic depicting the profile created within the distal-end region of the catheter when the steering system is in a retracted position such as shown in FIG. 4C.

DETAILED DESCRIPTION OF THE PREFERRED EMBODIMENTS

Figure 1:
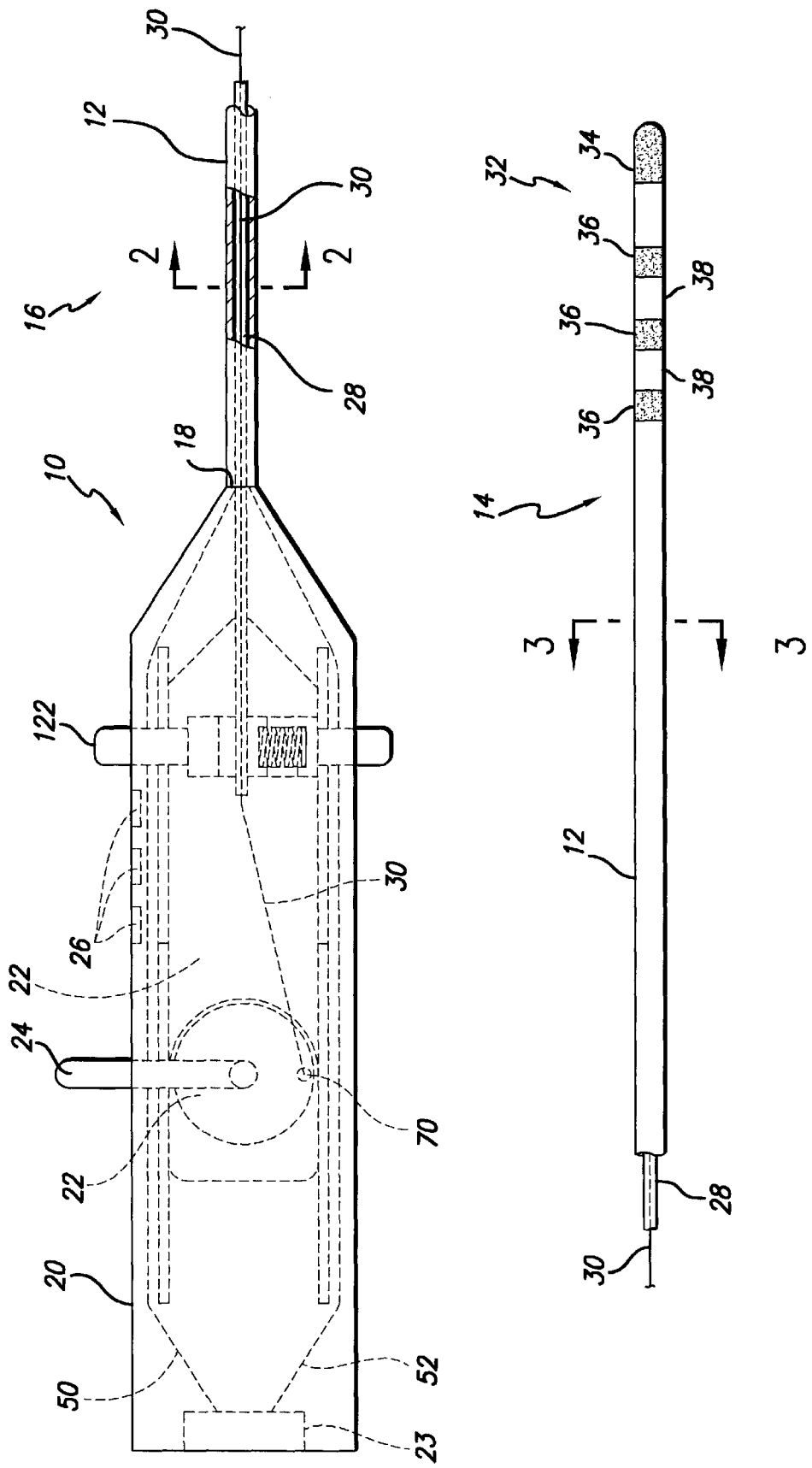
FIG. 1 is a plan view with a broken-out section of a catheter configured in accordance with the invention depicting the primary components of the catheter including a sheath, a positioning mechanism, and a steering system.

Referring now to the drawings, in which like reference numerals are used to designate like or corresponding elements among the several figures, in FIG. 1 there is shown a catheter 10 configured in accordance with aspects of the present invention. The catheter 10 includes a sheath 12 having a flexible distal-end region 14, a less flexible proximal-end region 16, and an inner lumen (not shown) spanning longitudinally throughout the sheath.

The proximal end 18 of the sheath 12 is secured to a handle 20. The handle 20 carries a controller 22, a lever 24, and a plurality of positioning slots 26. The handle 20 and controller 22 form a positioning mechanism that is movable along the positioning slots 26. Movement of the controller 22 within the handle 20 effects the position of the steering system, which in turn, as described further below, effects the steerable profile of the catheter 10. As also described in detail below, the lever 24 is part of a steering system which further includes a core base 28 and a tendon 30.

The distal end 32 of the sheath 12 includes a tip electrode 34 for applying ablation energy to a biological site (not shown). Located proximal from the tip electrode 34 are three band electrodes 36 arranged in a substantially linear array along the distal-end region 14 of the sheath 12. The band electrodes 36 are arranged so that there is space 38 between adjacent electrodes. In one configuration, the band electrodes 36 are three mm wide and the space 38 between the electrodes is four mm wide. The band electrodes 36 may be used to map the interior surfaces of the heart or to apply ablation energy, or both. The tip electrode 34 may be used to deliver RF energy to the biological site (not shown) to form spot or tip-drag lesions, or for mapping.

Referring to FIGS. 2A and 2B, the proximal-end region 16 of the sheath is a layered composite. The inner layer 40 is a tube formed of a polymer pocessing a high modulus of elasticity, such as polyetheretherketone (PEEK). The outer layer 42 is formed of a flexible. intermediate-durometer polymer such as polyether block amide, known commercially as Pebax™. In one particular embodiment, the outer layer 42 comprises a 63 D (shore "D" hardness value) hardness scale Pebax™ tube. Positioned between the inner layer 40 and the outer layer 42 is one or more layers of a braided ribbon 44 used to increase the torsional rigidity of the proximal-end region 16. Only one layer is shown in FIGS. 2A and 2B for clarity of illustration. The three layers 40, 42, and 44 are bonded together by the simultaneous application of heat and pressure, thus creating a flexible tube possessing superior torsional rigidity.

As shown in FIG. 2A, in one configuration of the catheter, positioned along the circumference on one side of the inner layer 40 is a groove 46. A separate groove 48 is positioned on the opposite side of the inner layer 40. The grooves 46, 48 span the length of the proximal-end region 16 (FIG. 1) from the handle 20 (FIG. 1) to the distal-end region 14 (FIG. 1). As explained below, the grooves 46, 48 are used to carry lead wires to the electrodes 34, 36. A lumen 82 for the steering tendon 30 (FIG. 1) is carried by the core base 28 and positioned perpendicular to the grooves 46/48. The core base 28 is surrounded by the three layer section of the proximal-end region 16 of the sheath 12.

Referring to FIG. 2B, in an alternative configuration of the catheter, the core base 29 is fabricated with two grooved indentations 83 on opposite sides which extend longitudinally along the length of the core base. A lumen 82 for the steering tendon 30 (FIG. 1) is offset perpendicular to the grooved indentations 83 within the core base 29. In both of FIGS. 2A and 2B, the lead wires and steering tendon are not shown for clarity of illustration.

With reference to FIG. 3, the construction of the distal-end region 14 is essentially the same as that of the proximal-end region 16 (FIG. 2A) except it does not include a middle stainless steel braided ribbon 44 (FIG. 2A) layer. In addition, the outer layer 43 has a thickness greater than the outer layer 42 (FIG. 2A) of the proximal-end region. The inner layer 41 has substantially the same thickness as the inner layer 40 of the proximal-end region. Because the distal-end region 14 does not include a braided ribbon 44 it has more relative flexibility than the proximal-end region 16 enabling it to more easily steer to conform to the selected biological site. Flexibility of the distal-end region 14 may be further increased by using a lower durometer material for the layers 41, 43.

Figure 4C:
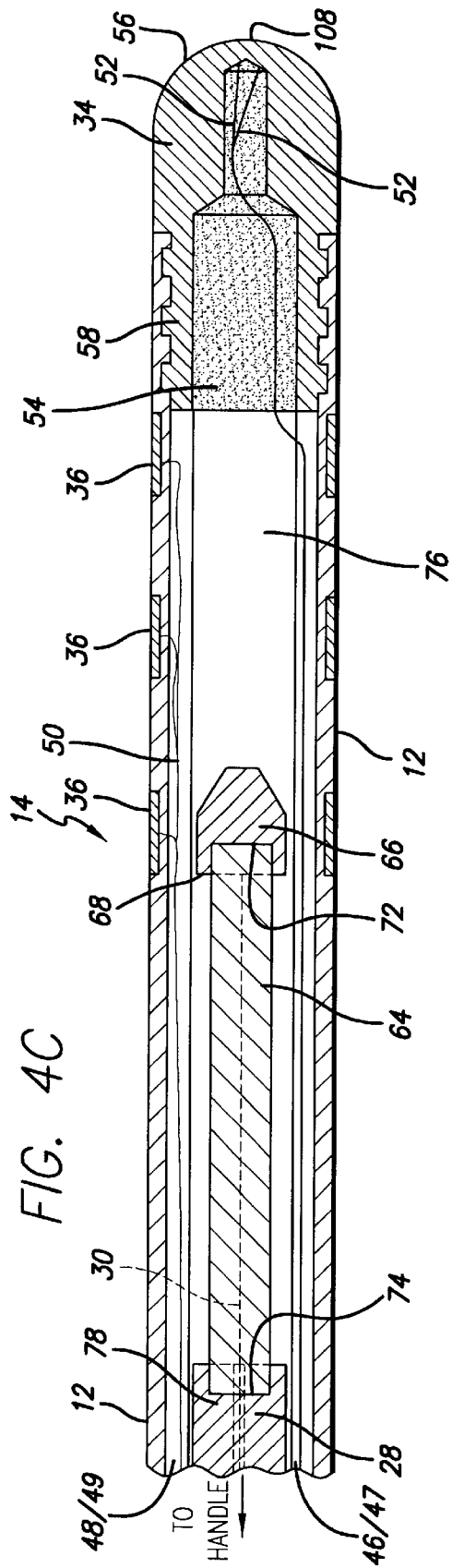
FIG. 4C is a cross section view of the distal portion of the catheter of FIG. 1 depicting detailed components of the catheter steering system in a partially retracted position.

With continued reference to FIG. 3, positioned along the circumference on one side of the inner layer 41 is a groove 47. A separate groove 49 is positioned on the opposite side of the inner layer 41. The grooves 47, 49 span the length of the distal-end region 14 and align with the grooves 46, 48 in the proximal-end region 16 (FIG. 2) to form continuous grooves that span the entire length of the sheath 12. As shown in FIGS. 4A and 4C, the grooves 46/47, 48/49 carry individual lead wires 50 and a pair of thermocouple wires 52 to the band electrodes 36 and the bore 54 within the tip electrode, respectively. In order to form one continuous sheath 12 (FIG. 1), the distal-end region 14 and the proximal-end region 16 are bonded together.

Referring to FIGS. 4A–C, the tip electrode 34 includes a substantially dome-shaped distal portion 56 and a substantially cylindrical proximal portion 58. The tip electrode 34 is formed of a biocompatible material having high thermal conductivity properties. Possible materials include silver, gold, chromium, aluminum, molybdenum, tungsten, nickel, platinum, and platinum/10% iridium.

The band electrodes 36 are also formed of a material having a significantly higher thermal conductivity than that of the biological tissue. Because of the difference in thermal conductivity between the band electrodes 36 and the tissue, the electrodes cool off more rapidly in the flowing fluids at the biological site. The band electrodes 36 are sized so that the surface area available for contact with fluid in the heart, e.g., blood, is sufficient to allow for efficient heat dissipation from the electrodes to the surrounding blood. In a preferred embodiment, the electrodes 36 are 7 French (2.3 mm in diameter) with a length of 3 mm.

Individual lead wires 50, as shown in FIGS. 4A and 4C, extend from a connector 23 (FIG. 1) at the distal end of the handle 20 to each band electrode 36. The lead wires 50 are attached to the band electrodes 36 in a way that establishes good electrical contact, such as by welding. The lead wires 50 are grouped together and span throughout one of two grooves 47, 49 within the distal-end region 14 and continue into the proximal-end region 16 (FIG. 1) of the sheath 12 through one of two grooves 46, 48. The sheath 60 is formed of a flexible material, such as a thin-walled heat-shrink tubing, so that it may bend as necessary.

With further reference to FIGS. 4A and 4C, a pair of thermocouple wires 52 run from the handle 20 (FIG. 1) through the sheath 12 to a bore 54 within the tip electrode 34. Each of the thermocouple wires 52 is separately attached at the distal end of the bore 54 in the tip electrode 34 in a way that maintains good electrical contact, such as by soldering. The attachment of the thermocouple wires 52 to the tip electrode 34 in this manner achieves the thermocouple effect through the tip electrode, and also achieves good thermal contact for a more accurate determination of the temperature of the tip electrode. Subsequent to being attached to the bore 54, the thermocouple wires 52 are potted into the bore with a resin, such as epoxy. One of the thermocouple wires 52 also serves as a drive wire to transmit ablation energy to the tip electrode 34. Exemplary configurations of electrodes having combination thermocouple/drive wires are disclosed in U.S. Pat. Nos. 6,049,737 and 6,045,550, the disclosures of which are hereby incorporated by reference. The thermocouple wires 52 are grouped together and span through one of two grooves 47, 49 within the distal-end region 14 and continue into the proximal-end region 16 of the sheath 12 through one of two grooves 46, 48.

With continued reference to FIGS. 4A and 4B, the steering system, in addition to the steering tendon 30 and the core base 28 mentioned above, includes a ribbon stylet 64, and a core distal tip 66, all of which are partially or entirely housed within the sheath 12. The core base 28 and core distal tip 66 are cylindrical and sized to allow for longitudinal movement within the sheath lumen 76. In a preferred embodiment, the diameter of the core distal tip 66 is the same as the core base 28. As previously mentioned, the steering system also includes a lever 24 (FIG. 1) positioned external the sheath 12 at the proximal end of the catheter 10. As shown most clearly in FIG. 4B, the distal end 68 of the tendon 30 is attached to the core distal tip 66, and is offset from the longitudinal axis of the sheath 12. The distal end 68 of the tendon 30 is secured to the proximal end of the core distal tip 66 such as by welding, soldering, brazing, adhering, or otherwise attached to the core distal tip 66. The tendon 30 extends longitudinally through the core base 28 through the lumen 82 to the handle 20 (FIG. 1). As shown in FIG. 1, the proximal end 70 of the steering tendon 30 exits through the proximal end 18 of the sheath 12, and attaches to the lever 24. The tendon 30 may be formed from stainless steel wire having a diameter of approximately 0.2 mm.

Referring again to FIGS. 4A and 4B, the stylet 64 includes a distal end 72 and a proximal end 74. The distal end 72 of the stylet 64 is attached to the core distal tip 66 at a first end and is secured thereto such as by welding, soldering, brazing or adhering. The stylet 64 extends longitudinally throughout the inner lumen 76 of the sheath 12 and is attached at its proximal end 74 to the core base 28. In a preferred embodiment, the stylet 64 is formed of a shape-memory alloy element which exhibits martensitic phase transformation. Some examples of alloys with the aforementioned properties include those which exhibit non-linear superelasticity (typically Ni—Ti with Ni at 49–51.5% atomic) and those which exhibit linear superelasticity (typically Ni—Ti in near equi-atomic composition which has been cold worked). It is preferable that the stylet 64 is formed of nitinol having a composition of 49–51.5% Ni. In one embodiment, the stylet 64 is circular in cross-section and has a diameter of 0.030 inches. In another embodiment, the stylet 64 is rectangular in cross-section and has a dimension of 0.008 inches×0.053 inches.

The core base 28 includes a distal end 78 and a proximal end 80 (FIG. 1), and is preferably a solid cylindrical member made from an extrudable polymer possessing a high elastic modulus. Exemplary of such polymers include polyetheretherketone (PEEK), polyimide, and polyetherimide (Ultem).

In a preferred embodiment, the core base 28 is sized to fit within the sheath lumen 76 with sufficient clearance to allow for longitudinal movement within the lumen. As previously mentioned, the core base 28 includes a lumen 82 offset from the center axis. The lumen 82 extends through the length of the core base 28 and carries the steering tendon 30. As shown in FIGS. 4A–C, the core base 28 is attached to the stylet 64 at its distal end 78. The distal end 78 of the core base 28 is positioned in the distal-end region 14 of the sheath 12. As explained further below, the core base 28 is able to move longitudinally throughout the inner lumen 76 of the sheath 12 with its position controlled by corresponding longitudinal movement of the controller 22. As shown in FIGS. 5A and 5B, the handle 20 has the proximal end 18 of the sheath 12 fixed thereto. The controller 22 is carried by the handle 20 and is attached to the core base 28 at its distal end 112. The core base 28 extends into the controller 22 and passes through a locking element 110. The core base 28 terminates just beyond the locking element 110 while the steering tendon 30 carried by the core base extends to the lever 24 where it is attached. The lever 24 is movable about an axis to effect axial displacement of the tendon 30 along the length of the sheath 12. The controller 22 is positioned between a pair of support plates 25 fixed to the handle 20. Situated along the exterior of the handle 20 is a series of slots 26 to secure a select position of the controller 22 by engaging the locking element 110 as it moves along the length of the handle 20 when advancing or retracting the steering system. The locking element 110 is positioned at the distal end 112 of the controller 22 and is locked and released by a spring-loaded button 122 that can engage in various locking positions. Although FIGS. 5A and 5B depict a series of four slots 25 positioned along the distal-end region 84 of the handle 20, the present invention is not limited to such as additional or fewer such slots may be used.

When the controller 22 is in an advanced position 86 (FIG. 5A), the internal portion of the steering system, i.e., the core base 28, stylet 64, and the core distal tip 66, is positioned as shown in FIG. 4A. When in this advanced position, the steering system, through rotation of the lever 24, is able to deflect the distal-end region 14 of the sheath 12 to assume the curve 88 as shown in FIG. 8.

When the controller 22 is in a retracted position 90 (FIG. 5B), the internal portion of the steering system, as mentioned above, is positioned as shown in FIG. 4C. When in this retracted position, the steering system is able to deflect the distal-end region 14 of the sheath 12 to assume a slightly curved shape 92 (FIG. 9) while the portion distal the core distal tip 66 does not curve.

Figure 6:
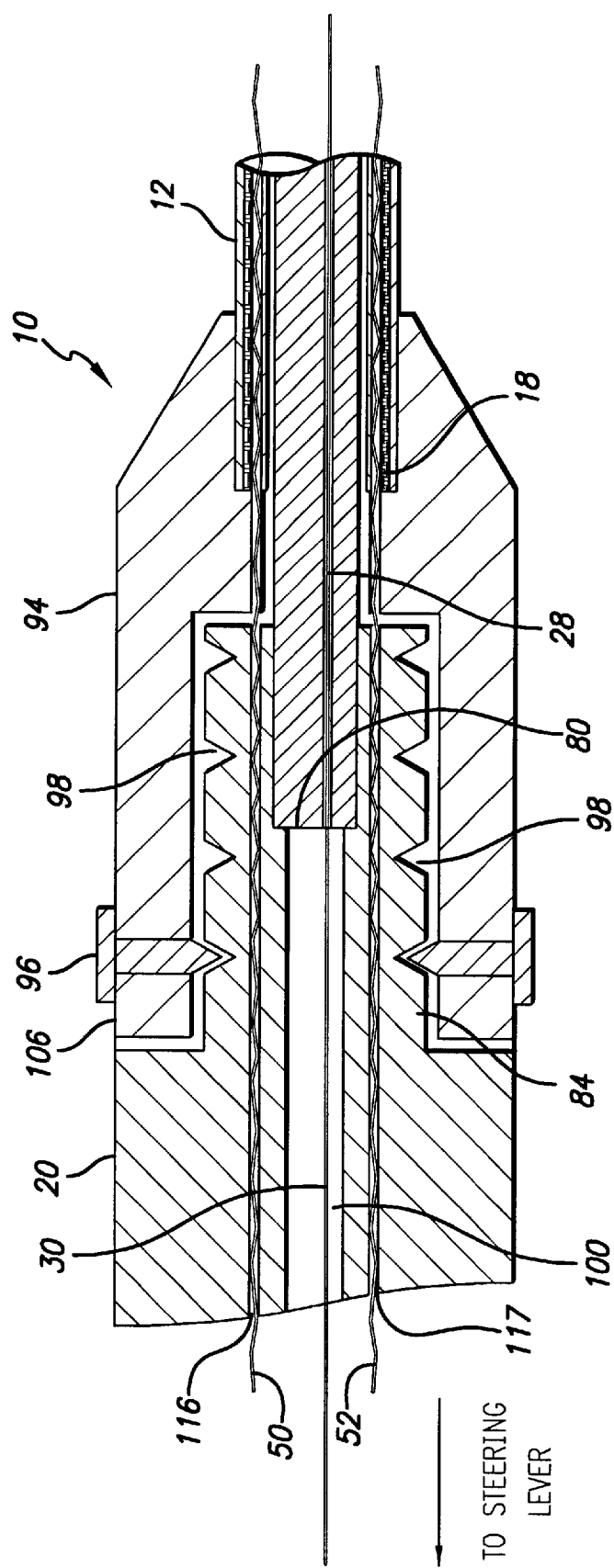
FIG. 6 is a cross section of an alternate configuration of the positioning mechanism shown in a retracted position and including an adjustable cap and a locking mechanism.
Figure 7:
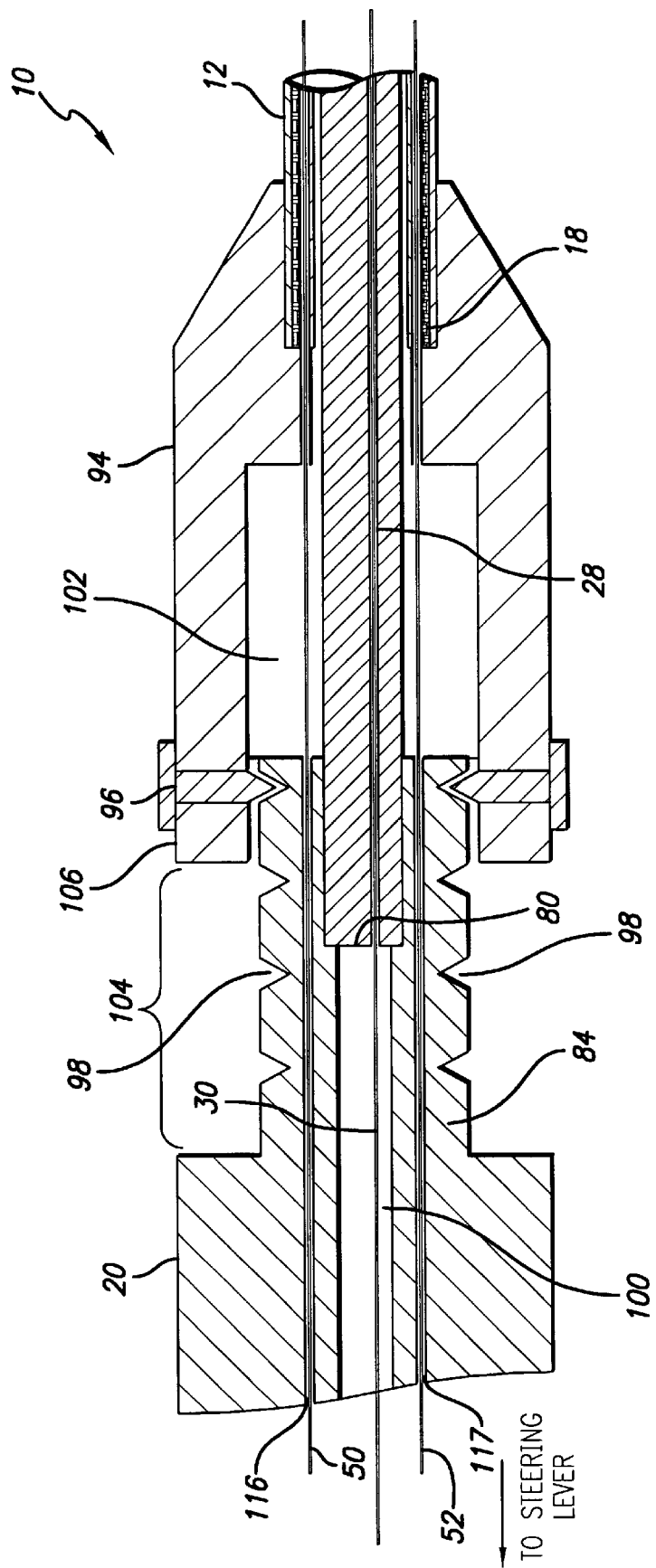
FIG. 7 is a cross section of the positioning mechanism of FIG. 6 in an advanced position.

Referring now to FIGS. 6 and 7, in an alternate configuration of the catheter 10, the positioning mechanism consists of an adjustable cap 94 which is fixed to the proximal end 18 of the sheath 12. The cap 94 is movable longitudinally along the length of the distal-end region 84 of the handle 20. While the cap 94 is movable, the steering system core base 28 is fixed to the handle 20 and hence does not move when the cap 94 is being positioned to a particular setting. The adjustable cap 94 includes one or more locking mechanisms 96 such as set screws, for securing the cap in place relative to the handle 20. The distal-end region 84 of the handle 20 carries a plurality of annular recesses 98 into which the set screws 96 may be tightened in order to lock the cap 94 in place. Although the figure only shows four recesses, in other configurations, additional recesses maybe included. The steering tendon 30 runs through the entire length of the core base 28 and exits from its proximal end 80. The tendon 30 continues to extend through the inner lumen 100 of the handle 20 towards a steering lever (not shown in FIG. 6 or 7), where it is attached.

Retraction of the cap 94 along the length of the handle 20 to a position as shown in FIG. 6, positions the internal portion of the steering system, i.e., the core base 28, stylet 64, and the core distal tip 66, as shown in FIG. 4A. In this position (FIG. 6) the adjustable cap 94 is locked into place in the innermost recess of the distal-end region 84 of the handle 20.

Advancement of the cap 94 along the length of the handle 20, as shown in FIG. 7, positions the internal portion of the steering system as shown in FIG. 4B. In this position (FIG. 7) the adjustable cap 94 is set in a fully advanced position with the set screws 96 locked in the most distal recess 98. With the advancement of the adjustable cap 94 along the length of the handle 20, the core base 28 remains in a fixed position in the distal-end region 84 of the handle 20. As the adjustable cap 94 is set in an advanced position, a space 104 separates the distal-end region 84 of the handle 20 from the proximal-end region 106 of the adjustable cap.

With further reference to FIG. 6, a lumen 116 extends through the length of the distal-end region 14 of the sheath 12, the adjustable cap 94, and the handle 20, carrying loosely coiled individual lead wires 50 from the electrode bands (not shown) while the cap is set in a fully retracted position. A lumen 117 on an opposite side extends from the distal end 32 of the sheath 12, through the length of the adjustable cap 94, and the handle 20, carrying the set of thermocouple wires 52 from the tip electrode 34 (not shown). The lead wires 50, 52 are coiled so as to provide the necessary slack to allow the adjustable cap 94 to move between retracted and advanced positions. As shown in FIG. 7, when the adjustable cap 94 is fully advanced, the wires 50, 52 within the lumens 116, 117 become taut. As the adjustable cap 94 is retracted, the wires 50, 52 assume their coiled shape.

In operation, as shown in FIGS. 4A and 4C, the profile of the distal-end region 14 of a catheter configured in accordance with the invention can be changed by altering the position of the steering system, particularly the core distal tip 66, relative to a catheter distal tip 108, and then applying tension to the tendon 30. When tension is applied to the tendon 30, the stylet 64 and core distal tip 66 are deflected toward the inner layer 41 of the sheath 12. The core distal tip 66 contacts the inner layer 41 and imparts lateral force to the sheath 12, thereby causing the distal-end region 14 of sheath 12 to curve. The greater the tension applied to the tendon the more pronounced the curve becomes. For example, by positioning the steering system as shown in FIG. 4A and applying tension, the distal-end region 14 of the sheath 12 may be made to assume the curve 88 as shown in FIG. 8. By positioning the steering system as shown in FIG. 4C and applying tension to the tendon 30 with the use of the steering lever 24, the distal-end region 14 of the sheath 12 may be made to assume a slightly curved shape 92, while the portion distal the core distal tip 66 does not curve as shown in FIG. 9. FIGS. 8 and 9 represent only two of many possible deflection profiles that may be obtained with the catheter. A variety of different profiles are available by adjusting the position of the steering system.

It will be apparent from the foregoing that, while particular forms of the invention have been illustrated and described, various modifications can be made without departing from the spirit and scope of the invention.

What is claimed is:

1. A catheter comprising:
    a sheath having a proximal end, a distal-end region and a lumen therebetween;
    a steering system for deflecting the distal-end region; and
    a positioning mechanism for adjusting the position of the steering system relative to the sheath;
    wherein the steering system comprises:
        a core slidably disposed within the lumen and having a distal end positioned in the distal-end region of the sheath;
        a lever located at the proximal end of the sheath; and
        a tendon located within the lumen having a first end attached to the core distal end and a second end attached to the lever; wherein the core comprises a distal tip and the first end of the tendon is attached thereto.

2. The catheter of claim 1 wherein the positioning mechanism may adjust the steering system to an advanced position to effect deflection at the distal end of the sheath distal-end region.

3. The catheter of claim 1 wherein the positioning mechanism may adjust the steering system to a retracted position to effect deflection at the proximal-end region of the sheath distal-end region.

4. The catheter of claim 1 wherein the core further comprises:
    a core base proximal the distal tip; and
    a stylet extending between the core base and the core distal tip.

5. The catheter of claim 4 wherein the core distal tip is fixed to the distal end of the stylet and the proximal end of the stylet is fixed to the distal end of the core base.

6. The catheter of claim 2 wherein the positioning mechanism comprises:
    a handle having the proximal end of the sheath fixed thereto; and
    a controller carried by the handle and attached to the core and the lever and the tendon, the controller movable longitudinally along the distal-end region of the handle.

7. The catheter of claim 6 wherein the controller comprises:
    a locking element fixed to the core, the locking element movable longitudinally along the distal-end region of the handle;
    wherein the locking element is housed within the handle and is locked and released by a spring-loaded button that can engage in various locking positions.

8. The catheter of claim 7 wherein the distal-end region of the handle carries a plurality of positioning slots that interact with the locking element.

9. A catheter comprising:
    a sheath having a proximal end, a distal-end region and a lumen therebetween;
    a core slidably disposed within the lumen and having a distal end positioned in the distal-end region of the sheath;
    a tendon located within the lumen having a first end attached to the core distal end and a second end exiting the proximal end of the sheath;
    a handle having the proximal end of the sheath fixed thereto; and
    a controller carrying a lever having the proximal end of the tendon attached and movable to effect axial displacement of the tendon, the controller carried by the handle and having the core attached thereto, the controller movable longitudinally along the distal-end region of the handle.

10. The catheter of claim 9 wherein longitudinal movement of the controller in the distal direction advances the core in the distal direction.

11. The catheter of claim 9 wherein longitudinal movement of the controller in the proximal direction retracts the core in the proximal direction.

* * * * *